United States Patent [19]
Hohberger

[11] 3,945,297
[45] Mar. 23, 1976

[54] MACHINE TOOL SPINDLE CALIBRATION METHOD AND APPARATUS

[75] Inventor: Clive P. Hohberger, Port Jefferson, N.Y.

[73] Assignee: Allen-Bradley Co., Milwaukee, Wis.

[22] Filed: Apr. 15, 1974

[21] Appl. No.: 460,802

Related U.S. Application Data

[62] Division of Ser. No. 268,743, July 3, 1972, Pat. No. 3,827,293.

[52] U.S. Cl. .................. 90/11 C; 82/2 B; 318/571
[51] Int. Cl.² ..................... B23Q 11/04; G05B 5/00
[58] Field of Search ...... 90/11 C, 11 R, 11 E, 13 C, 90/DIG. 28, DIG 12; 82/2 B; 33/88 R, 1 B, 89; 318/571

[56]  References Cited
UNITED STATES PATENTS

| | | |
|---|---|---|
| 2,498,881 | 2/1950 | Eldridge, Jr. ..................... 73/133 R |
| 3,602,090 | 2/1970 | Whetham ........................... 90/13 C |
| 3,698,268 | 10/1972 | Cutler ................................. 82/2 B |
| 3,746,955 | 3/1971 | Kobayashi .......................... 82/2 B |

Primary Examiner—Donald R. Schran
Attorney, Agent, or Firm—Lindenberg, Freilich, Wasserman, Rosen & Fernandez

[57] ABSTRACT

A simple method and apparatus is disclosed for the calibration of a numerically controlled milling machine or the like, to determine the compliance for a particular set-up of the machine. The apparatus includes a hydraulic cylinder mounted on the machine bed, with the end of the hydraulic piston bearing against a non-rotating cutting tool that is mounted in the spindle. A pressure gauge or pressure switch indicates fluid pressure in the hydraulic cylinder to determine force of the piston on the cutting tool, and a deflection sensor measures the static deflection of the spindle. In one apparatus, hydraulic fluid from a high pressure source passes through a pressure-reducing valve into the rear of the hydraulic cylinder to push the piston rod end against the cutting tool, without requiring motion of the spindle relative to the bed, the valve being adjusted to maintain a desired fluid pressure behind the piston despite leakage of fluid past the piston.

3 Claims, 6 Drawing Figures

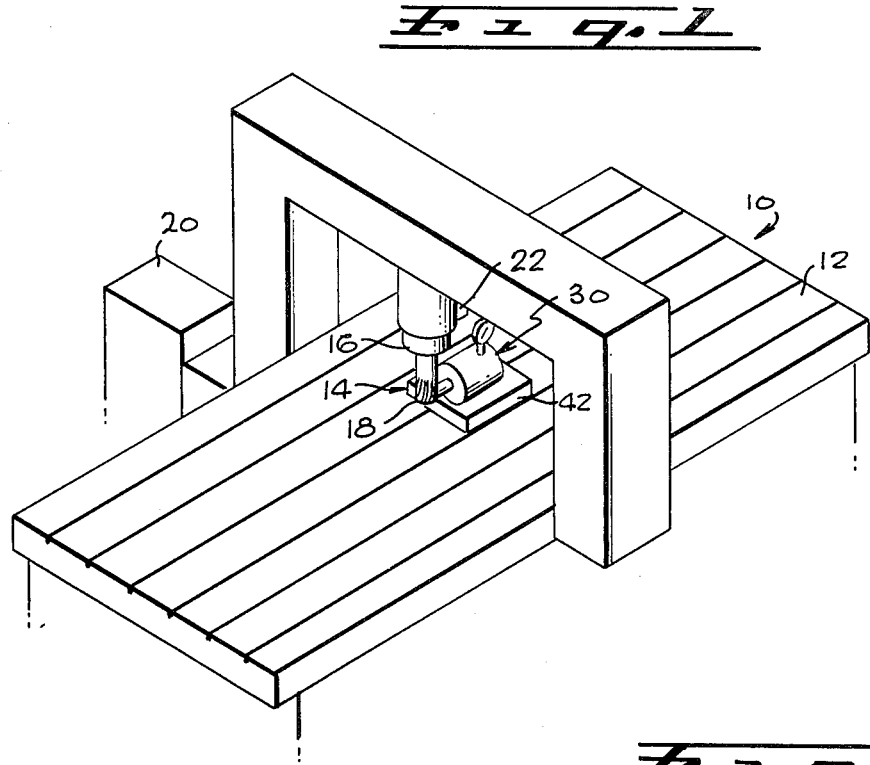
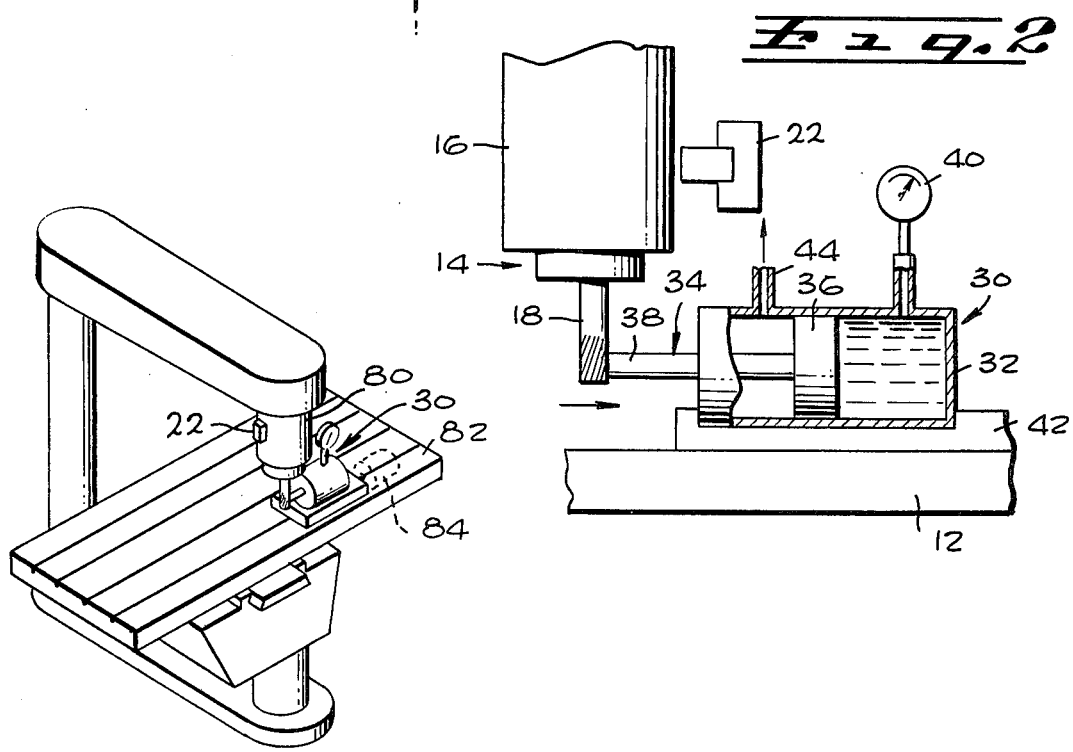

MACHINE TOOL SPINDLE CALIBRATION METHOD AND APPARATUS

This is a division, of application Ser. No. 268,743, filed July 3, 1972, now U.S. Pat. No. 3,827,293.

BACKGROUND OF THE INVENTION

This invention relates to apparatus for measuring the static cutter compliance of a machine tool.

It is generally desirable to operate numerically controlled machine tools and the like att the highest possible feed rate. The feed rate is often limited by the maximum force which the cutting edge of the cutting tool can apply to the work without causing breakage of the cutter. In finishing operations, the feedrate must also be maintained below a certain level to keep the surface roughness of the finished work surface below a predetermined level.

Direct measurement of the force on the cutting edge of the tool is desirable but not always attainable in practice. Instead of measuring force on the cutter, some machines measure deflection produced by the force on the cutter. Some machines have deflection sensors that measure the deflection of the spindle during cutting to limit the feed rate. In order to determine the force on the cutting tool with such sensors, it is necessary to determine the compliance of the spindle/tool system, or in other words, the relationship between the force on the cutting tool and the deflection sensed by the spindle deflection sensor. This relationship varies according to the particular cutter used, the method of cutter mounting on the spindle, the location and length therealong at which it contacts the work, and other factors. Thus, it is generally desirable to calibrate the compliance of the spindle apparatus for each particular cutting tool set-up.

The on-line calibration of compliance can be accomplished by applying a known force at a location on the machine system near the active region of the nonrotating cutter and measuring the spindle deflection. It is desirable that any such force-applying apparatus be accurate to at least a few percent, and that it retain such accuracy in spite of a relatively hostile environment encountered in actual usage, where dirt, oil, coolant, chips, and the like may be present and where the calibration apparatus may be subjected to rough handling.

SUMMARY OF THE INVENTION

In accordance with one embodiment of the present invention, an apparatus and method is provided for measuring the compliance of a machine system, which is simple and which maintains its accuracy under the conditions encountered in a machining environment. A cutting tool is mounted in the spindle of the machine, and a force measuring apparatus which includes a hydraulic cylinder is mounted on the bed of the machine with the rod end of the piston disposed against a region of the non-rotating cutter that will encounter the work in actual machining. A pressure gauge connected to the cylinder measures the pressure of hydraulic fluid therein, to indicate the force of the piston on the cutter. The spindle can be moved against the outer end of the piston to increase the force and therefore the fluid pressure. When the force reaches a predetermined level, the amount of spindle deflection is read from a deflection sensor and entered into the machine control as a measurement of the static cutter compliance.

In another embodiment of the invention, the spindle and machine bed are not moved towards one another, but instead hydraulic fluid is pumped into the hydraulic cylinder so that the piston is moved against the non-rotating cutter. Fluid from a high-pressure source flows through a pressure reduction valve into the hydraulic cylinder, and pressure in the hydraulic cylinder is read from a gauge. Although fluid may leak past the piston, the pressure reduction valve is opened to an extent that allows for replenishment of the leaked fluid while maintaining the desired pressure on the piston and thus a predetermined force on the non-rotating cutter. The external supply of pressured fluid allows for a higher rate of leakage past the piston, permitting lubrication so that the friction of the piston on the cylinder can be maintained at a low level. The movement of the piston by a constant flow of fluid to the cylinder also simplifies measurements, because it eliminates the need for actively moving the spindle or bed during measurements, and for closely controlling the initial position of the cutter relative to the piston rod end.

The novel features of the invention are set forth with particularity in the appended claims. The invention will best be understood from the following description when read in conjunction with the accompanying drawings.

BRIEF DESCRIPTION OF THE DRAWINGS

FIG. 1 is a perspective view of calibration apparatus constructed and utilized in accordance with the invention;

FIG. 2 is a partial side elevation view of the apparatus and method illustrated in FIG. 1;

FIG. 3 is a perspective view of the calibration apparatus of FIG. 1, shown utilized on another type of machine;

DESCRIPTION OF THE PREFERRED EMBODIMENTS

Figure 4:
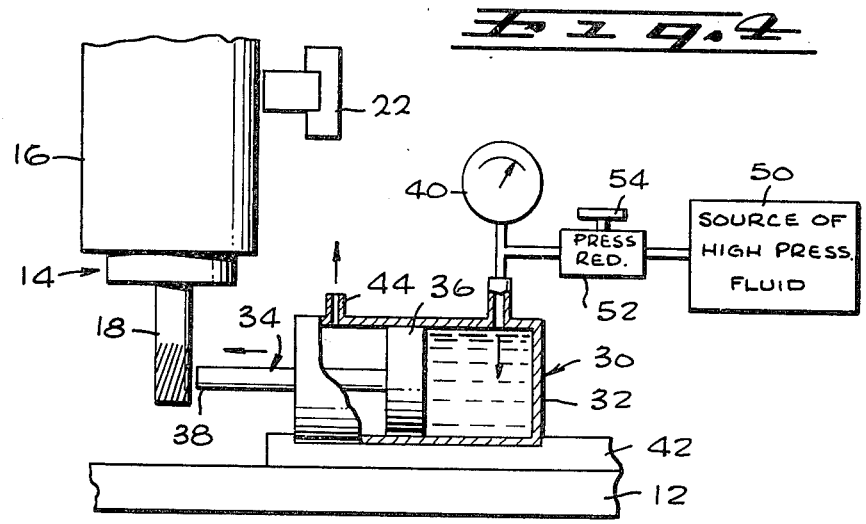
FIG. 4 is a partial side elevation view of a calibration apparatus and method in accordance with another embodiment of the invention.

FIG. 1 illustrates a milling machine 10 which includes a bed 12 for holding work that is to be machined, and a spindle apparatus 14 that includes a spindle 16 and cutter 18 for machining the work. The spindle apparatus 14 can move along the bed, and its movements are controlled by a milling machine controller 20. The machine includes a sensor 22 that measures deflection of the spindle apparatus in one direction, to provide feedback for the milling machine controller 20. Force on the cutter 18 produces a deflection at the spindle that the deflection sensor 22 can sense, and the milling machine controller 10 can be designed and/or programmed to control the feed rate so that the force on the cutter can be maintained at or held below a predetermined level. However, this requires that the relationship be known between force on the cutter 18 and deflection as measured by the deflection sensor 22.

The compliance, or relationship between force on the cutter 18 and deflection measured by the deflection sensor 22, varies for different tooling set-ups. The diameter of the cutter, number of cutting edges, the method of attachment to the spindle, the amount by which the cutter projects from the spindle, and the portion of the cutter that contacts the work, are among the factors affecting the relationship between force on the cutter and the measured deflection of the spindle apparatus. Thus, it is often useful to measure this relationship on-line, that is, for the actual tooling set-up tto be used in machining. By applying a known force to the cutter 18, measuring the resulting spindle deflection as sensed by the sensor 22, and entering this into the milling machine controller 20, it is possible to design and/or program the milling machine controller 20 in a manner so as to achieve efficient utilization of the machine while maintaining the required tolerances and cutter life for the actual operations to be performed.

A variety of devices can be utilized to apply a desired high level of force to the spindle apparatus 14. However, many of the devices that can be utilized cannot withstand the rough usage and hostile environment encountered in the machining area of a machine tool. The machining area is likely to contain dirt, oil, coolants, chips and the like that can interfere with any delicate mechanisms and limit their accuracy over an extended period. Furthermore, the apparatus must withstand considerable handling, since it may have to be mounted and then removed each time the machine set-up is changed.

In accordance with the present invention, a hydraulic cylinder apparatus 30 is provided which can be mounted on the bed 12 of the machine to provide the required force to the spindle apparatus, and particularly to the cutter 18. As shown in FIG. 2, the cylinder apparatus 30 includes a hydraulic cylinder 32 and a piston 34 which can slide along the cylinder. The piston 34 has a rearward end portion 36 which slides within the cylinder, and an outer rod end 38 which can bear against the cutter 18 of the spindle apparatus 14. A pressure gauge 40 is mounted on the cylinder at a location behind the rear end 36 of the piston, to measure the fluid pressure behind the piston.

In order to measure the compliance of the cutter 18 mounted on the spindle apparatus 14, the non-rotating cutter 18 is moved towards the outer rod end 38 of the piston 34 while the cylinder apparatus 32 is firmly mounted by a bracket 42 on the machine bed 12. As the spindle apparatus moves towards the cylinder, the cutter 18 pushes the piston 34 in a direction to compress the fluid in the hydraulic cylinder 32. The fluid pressure in the cylinder 32, which is indicated by the gauge 40, is proportional to the force applied by the cutter 18 to the piston rod end 38. If desired, the dial of the pressure gauge 40 can be marked in units of force applied to the cutter 18. When a predetermined force is reached, as indicated by the gauge 40, the deflection of the spindle apparatus is measured by the deflection sensor 22. The compliance is proportional to the ratio of the spindle deflection to the force applied by the cutter 18. This measurement can be entered into the controller 20, to determine how the controller operates the drive that translates the spindle relative to the bed. For example, the controller can limit the feedrate of the spindle so that the deflection sensed by the sensor 20 does not exceed a level at which the force on the tool would be excessive.

After the compliance measurement is taken, a workpiece can be mounted on the machine bed 12 and machining can proceed. The cutting tool is preferably held at substantially the same position in the spindle during machining as during compliance measuring, and the same portion of the cutter which contacted the piston during measuring preferably contacts the work during machining. The controller 20 can be constructed by utilizing a common variable speed milling machine drive which includes a lead-screw motor that turns a lead-screw which advances the workpiece-holding bed 12. Where the speed of the lead-screw motor depends upon the current applied to it and the spindle deflection sensor is a strain gauge whose resistance increases with spindle deflection, the feed rate is controlled by applying a voltage across the strain gauge, amplifying the current through the strain gauge, and applying the amplified current to the motor. As spindle deflection increases, less current is applied to the motor so its speed cannot increase past a predetermined value. The motor speed for a given spindle deflection, is determined by varying the voltage across the strain gauge. An even simpler method of practicing the invention is for the machinist to write down the deflection measurement during calibration. During actual machining, the machinist begins cutting at a low feed rate and continually increases the feed rate until the deflection reaches the limit. Of course, the deflection can be merely read on a meter which senses the output of a strain gauge or proximity sensor. Closer control of operation can often be achieved by a computer-controlled controller, but either of the above two methods could instead be used.

When a force is applied to the piston 34 of the hydraulic cylinder apparatus 30, some hydraulic fluid will leak around the rearward end portion 36 of the piston to the region in front of this portion. Such leakage can be easily exhausted through a pipe 44 that leads to a fluid reservoir, or can be allowed to accumulate in front of the piston rearward portion 36. However, the constant leakage of fluid results in the necessity for constantly moving the spindle apparatus 14 in order to maintain the predetermined fluid pressure in the hydraulic cylinder. It would be somewhat easier to take measurements if the spindle apparatus did not have to be moved or if the pressure dropped only very slowly when the spindle movement stopped. This can be achieved by utilizing a hydraulic cylinder apparatus with a tighter sealing piston. However, if the piston is made to fit tighter its friction with the walls of the cylinder may also increase and this results in lower accuracy. FIG. 4 illustrates an apparatus and method constructed in accordance with another embodiment of the invention for facilitating measurements while maintaining accuracy.

In the apparatus of FIG. 4, a source 50 of high pressure hydraulic fluid is utilized to provide a constant flow of hydraulic fluid into the cylinder 32 of the cylinder apparatus 30. This flow of hydraulic fluid into the cylinder 32 can be utilized to move the piston 34 against the cutter 18 of the spindle apparatus 14 to provide the required contact force. The constant flow of fluid makes up for the fluid that leaks past the rearward portion 36 of the piston, so that the applied force on cutter 18 is maintained despite leakage around the piston rearward portion 36. The mechanism is utilized by mounting the cylinder apparatus 30 on the bed 12 of the machine, with the cutter rod end 38 of the piston adjacent to the cutter 18 of the machine tool. However, instead of moving the spindle apparatus 14 (or the bed 12 in the case of machine tools wherein the bed is moved), both the spindle apparatus 14 and bed 12 are maintained stationary. A pressure reduction valve 52 which connects the source of high pressure fluid 50 to the cylinder is opened to a degree necessary to allow hydraulic fluid to flow into the cylinder and move the outer rod end 38 of the piston 34 against the cutter 18. A control 54 on the pressure reduction valve 52 is adjusted so that the pressure read on the gauge 40 remains at the desired force level at which measurements of the deflection sensor 22 are to be taken. Hydraulic fluid will continue to leak past the rearward portion 36 of the piston and be exhausted through the line 44. However, such leakage will be constantly made up by new fluid flowing into the region behind the piston to maintain the desired pressure in the cylinder. The pressure reduction valve 52 is adjusted to provide for this.

The pressure reduction valve 52 allows a source 50 of high pressure hydraulic fluid to be utilized to operate the force-producing device. Sources of high pressure hydraulic fluid are often readily available in machine shops, so that generally a separate source does not have to be purchased to be used with the calibration apparatus. The pressure reduction valve 52 enables the reduction of fluid pressure and control of fluid flow from the high pressure source 50 to the required pressure level. This provides sufficient fluid flow for slowly moving the piston outer rod end 38 against the cutter 18 and, when motion stops, for thereafter maintaining the pressure in the hydraulic cylinder 32 and the force on cutter 18 at a desired level. The fact that hydraulic fluid can be constantly flowed into the cylinder means that a cylinder apparatus with a relatively loosely fitting piston can be utilized to minimize friction of the piston on the cylinder walls and to assure reliable operation under a wider variety of conditions (e.g. temperature changes, or the iclusion of dissolved air and/or small dirt particles in the hydraulic fluid).

Figure 5:
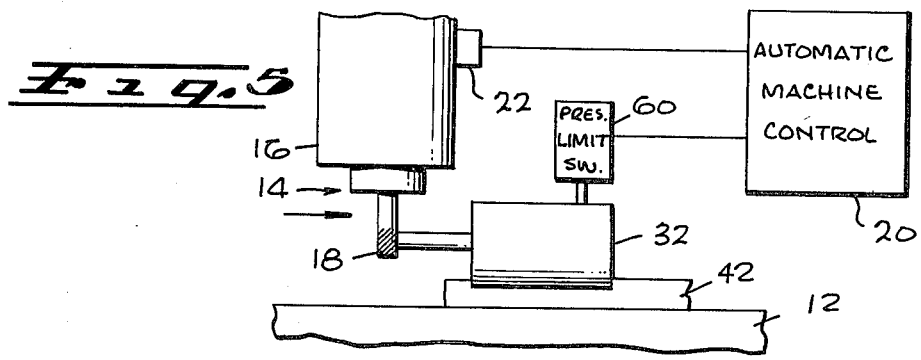
FIG. 5 is a partial side elevation view of still another embodiment of the invention.

The automatic measurement of compliance by a milling machine controller 20 can be accomplished automatically by apparatus of the type shown in FIG. 5. This apparatus is similar to that of FIG. 2, except that instead of a gauge, a pressure limit switch 60 is utilized that is connected directly to the milling machine controller 20. The pressure limit switch 60 is set to operate at a predetermined pressure level in the hydraulic cylinder 32 corresponding to the predetermined force on the cutter 18. When the pressure limit switch 60 operates, the milling machine controller 20 reads the deflection from the deflection sensor 22. In many applications, a pressure transducer may be utilized in place of the pressure limit switch 60, and the controller 20 can be constructed or programmed to note the pressure and deflection measurement at a certain point. For example, the controller may read the output of the sensor 22 when a particular pressure level is reached. Of course, a setup of the type illustrated in FIG. 4 can be utilized, with a pressure limit switch or transducer employed instead of (or in addition to) a single gauge.

Figure 6:
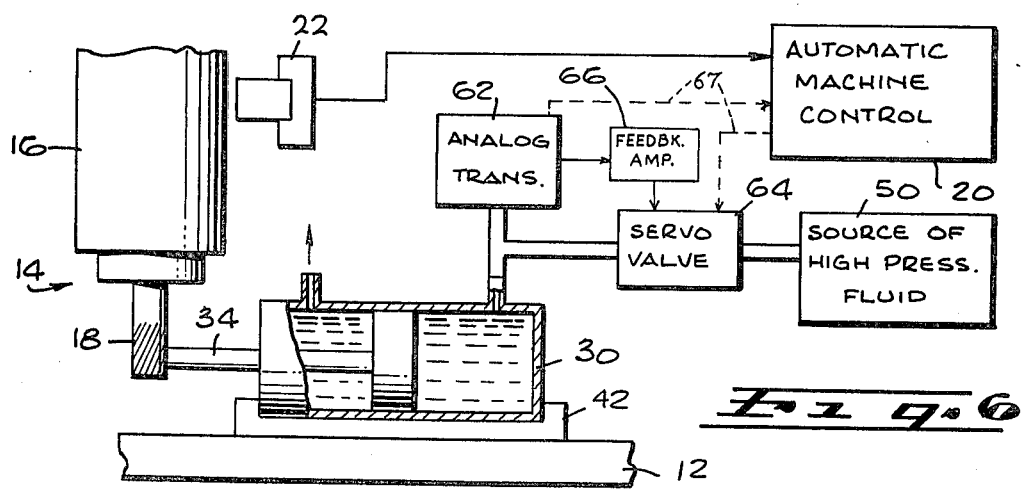
FIG. 6 is a partial side elevation view of yet another embodiment of the invention.

FIG. 6 illustrates another apparatus and method for the automatic measurement of compliance by a controller 20. This apparatus is similar to that of FIG. 4, except that instead of a gauge, an analog pressure transducer 62 is utilized, and instead of a mechanically adjustable pressure reducing valve, a valve 64 is utilized whose degree of opening can be controlled by an electrical or other signal, such valves often being referred to as servo valves. The analog-pressure transducer 62 generates an electrical signal which passes through a negative feedback servo amplifier 66 to the servo valve 64. So long as the pressure in the cylinder 32 is low, the output of the transducer 62 is low and the servo valve remains open to allow fluid to flow into the cylinder and move the piston 34. When the piston bears against the cutter 18 and the fluid pressure rises, the output of the transducer 62 increases and the opening of the servo valve decreases. The apparatus maintains a preset fluid pressure in the cylinder, at which the valve 64 is opened only far enough to make up for fluid leakage at that pressure. Once equilibrium is established, the controller 20 can be commanded to read the deflection sensed by the deflection sensor 20. The particular pressure at which equilibrium will be established can be varied by adjusting the gain of the amplifier 66. Instead of completing the feedback circuit through the amplifier 66, the circuit can be completed through the automatic machine control 20 through lines 67 so that the machine control determines the pressure to be maintained.

Thus, the invention provides a simple and reliable apparatus and method for applying a measured force to a spindle apparatus or other tool holding means to measure the compliance of a set-up. The use of hydraulic cylinders enables the maintenance of accuracy even in the hostile environment at the cutting area and in spite of rough handling. The reliability is achieved with an apparatus which is relatively simple and inexpensive. In one embodiment of the invention wherein the hydraulic cylinder is passive, the apparatus involves only a simple hydraulic cylinder and pressure gauge or pressure limit switch and means for mounting it on the bed of the machine tool. In another embodiment of the invention, which facilitates measurements by not requiring movement of the spindle apparatus or bed, the only addition to the apparatus is a controllable pressure reduction valve and a line for connecting it to a source of hydraulic fluid such as is commonly found in machine shops. The compliance measurement can be taken in a variety of machine tool types. For example, FIG. 3 illustrates another milling machine of a type wherein movement of a spindle relative to a bed 82 is accomplished by moving the bed, as by operating an axis feed drive 84 on the machine. The apparatus and method also can be applied to shapers, planers, lathes and a variety of other machines.

Although particular embodiments of the invention have been described and illustrated herein, it is recognized that modifications and variations may readily occur to those skilled in the art and consequently it is intended that the claims be interpreted to cover such modifications and equivalents.

What is claimed is:

1. A method for accurately operating a machine tool that includes a workpiece-holding bed, as rotatable spindle, a drive that produces relative translation of the spindle to the bed, a spindle deflection sensor, and a machine control which controls the drive, comprising:
   mounting a cutter on said spindle;
   mounting force measuring apparatus on said bed of said machine tool;
   creating movement of said spindle apparatus relative to said bed so that a predetermined portion of said cutter contacts and is forced against said force measuring apparatus;
   measuring the deflection of said spindle sensed by said spindle deflection sensor when said force measuring apparatus is forced against said cutter;
   mounting a workpiece on said bed;

rotating said cutter while it is held in substantially the same position on said spindle as it had when it contacted said force measuring apparatus; and operating said machine control to move said cutter into said workpiece at a rate which causes said spindle to be deflected by an amount which is a predetermined ratio of the deflection of said spindle which was sensed when said force measuring apparatus was forced against said cutter.

2. A method for accurately operating a machine tool that includes tool holding means for holding a cutter tool, a workpiece holder, and a drive that produces relative translation of the tool holding means to the workpiece holder, comprising:

mounting a cutting tool in said tool holding means;

mounting a force indicating apparatus having a force-receiving member, on said workpiece holder of said machine with the force-receiving member adjacent to said cutting tool;

creating movement of said tool holding means relative to said force-receiving member so that said force-receiving member receives force from said cutting tool;

monitoring the force indicated by said force indicating apparatus;

measuring the deflection of said tool holding means produced by said force on said force-receiving member and cutting tool, and recording the deflection value when said force indicating apparatus indicates a predetermined force level;

mounting a workpiece on said workpiece holder; and operating said drive to create relative movement of said cutting tool to said workpiece so that the cutting tool moves into the workpiece, while monitoring the deflection of said tool holding means, said drive being operated at a rate limited so that the deflection of the tool holding means does not exceed a value dependent upon said deflection value recorded when said force indicating apparatus indicated said predetermined force level.

3. A method for accurately operating a machine tool that includes a workpiece - holding bed, a spindle apparatus which includes a rotatable spindle, and a drive that produces relative translation of the spindle apparatus to the bed, comprising:

mounting a cutting tool in said tool holding means;

mounting a hydraulic cylinder apparatus which includes a hydraulic cylinder member and hydraulic piston member, on said bed, with a predetermined one of said hydraulic members adjacent to said cutting tool;

creating movement of said predetermined hydraulic member relative to said cutting tool while said spindle is substantially nonrotating, so that said cutting tool and predetermined hydraulic member apply force to each other;

measuring the pressure of fluid in said hydraulic cylinder to thereby measure the level of force of the cutting tool on the predetermined hydraulic member;

measuring the deflection of said spindle apparatus at a predetermined level of force of the cutting tool on the predetermined hydraulic member;

mounting a workpiece on said bed;

rotating said spindle to rotate the cutting tool; and measuring the deflection of said spindle apparatus while operating said drive at a rate which is limited to a rate that produces spindle apparatus deflection of the value occuring at the time when said predetermined level of force was produced at the cutting tool and the predetermined hydraulic member.

* * * * *